(12) United States Patent
Bouvier (10) Patent No.: US 9,259,203 B2
(45) Date of Patent: Feb. 16, 2016

(54) SYSTEM AND METHOD TO AUTOMATIC ASSIST POSITIONING OF SUBJECT IN MOBILE IMAGE ACQUISITION

(75) Inventor: Bernard Bouvier, Buc (FR)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 688 days.

(21) Appl. No.: 12/766,591

(22) Filed: Apr. 23, 2010

(65) Prior Publication Data

US 2010/0299014 A1    Nov. 25, 2010

(30) Foreign Application Priority Data

May 22, 2009   (FR) ...................................... 09 53407

(51) Int. Cl.
*G01C 22/00* (2006.01)
*A61B 6/00* (2006.01)

(52) U.S. Cl.
CPC ............... *A61B 6/547* (2013.01); *A61B 6/4405* (2013.01); *A61B 6/548* (2013.01)

(58) Field of Classification Search
USPC ............ 701/400, 408, 23, 25, 28; 5/600–601, 5/607–613, 616; 378/193, 197–198, 204, 378/208–209; 180/167–168; 600/407–408, 600/415, 417
See application file for complete search history.

(56) References Cited

U.S. PATENT DOCUMENTS

| | | | |
|---|---|---|---|
| 4,280,412 A | 7/1981 | Mihirogi | |
| 4,336,858 A | 6/1982 | Loyzim | |
| 4,411,100 A | 10/1983 | Suimon | |
| 4,484,666 A | 11/1984 | Steinmetz et al. | |
| 4,589,126 A * | 5/1986 | Augustsson et al. | 378/209 |
| 4,935,949 A * | 6/1990 | Fujita et al. | 378/198 |
| 5,013,018 A * | 5/1991 | Sicek et al. | 5/601 |
| 5,490,297 A * | 2/1996 | Bradcovich et al. | 5/601 |
| 5,572,569 A * | 11/1996 | Benoit et al. | 378/209 |
| 6,040,637 A * | 3/2000 | Paganini | B60R 21/01566 280/728.1 |
| 6,374,937 B1 * | 4/2002 | Galando et al. | 180/211 |
| 6,814,490 B1 * | 11/2004 | Suhm et al. | 378/198 |
| 7,173,265 B2 | 2/2007 | Miller et al. | |
| 7,450,682 B2 * | 11/2008 | Schonborn et al. | 378/4 |
| 7,695,192 B2 | 4/2010 | Henderson et al. | |
| 7,696,499 B2 | 4/2010 | Miller et al. | |
| 8,177,430 B2 * | 5/2012 | Bouvier | 378/198 |

(Continued)

FOREIGN PATENT DOCUMENTS

| | | |
|---|---|---|
| CA | 2229347 A1 | 8/1999 |
| DE | 102005004642 A1 | 8/2006 |

(Continued)

OTHER PUBLICATIONS

Search Report from corresponding EP Application No. 11163283.2 dated Sep. 7, 2011.

(Continued)

*Primary Examiner* — Redhwan K Mawari (57) ABSTRACT

A method of and system to perform image acquisition of a subject supported from a floor is provided. The system includes an imaging system and a table system having a tabletop in support of the subject from the floor. The table system also includes a mobile device having a drive to automatically transport the table system across the floor, identify a current position and to calculate a path relative to a reference to a pre-programmed target position for image acquisition.

20 Claims, 7 Drawing Sheets

(56) References Cited

U.S. PATENT DOCUMENTS

| | | | |
|---|---|---|---|
| 2001/0044577 A1* | 11/2001 | Braun et al. | 600/417 |
| 2005/0020906 A1* | 1/2005 | Seijger et al. | 600/415 |
| 2005/0065675 A1* | 3/2005 | Georgi et al. | 701/23 |
| 2005/0103545 A1* | 5/2005 | Green et al. | 180/168 |
| 2006/0002511 A1 | 1/2006 | Miller et al. | |
| 2007/0003021 A1 | 1/2007 | Guertin et al. | |
| 2007/0192910 A1 | 8/2007 | Vu et al. | |
| 2008/0042076 A1 | 2/2008 | Miller et al. | |
| 2008/0071420 A1* | 3/2008 | Guertin et al. | 700/228 |
| 2008/0194942 A1* | 8/2008 | Cumpson et al. | 600/415 |
| 2009/0070936 A1 | 3/2009 | Henderson et al. | |
| 2009/0082661 A1* | 3/2009 | Saladin et al. | 600/415 |
| 2010/0172468 A1* | 7/2010 | Gregerson | 378/20 |
| 2010/0296632 A1 | 11/2010 | Bouvier | |
| 2010/0299015 A1* | 11/2010 | Bouvier | 701/26 |
| 2010/0329426 A1 | 12/2010 | Oda et al. | |

FOREIGN PATENT DOCUMENTS

| | | | |
|---|---|---|---|
| JP | 6181104 A | 4/1986 | |
| JP | 11292278 | 10/1999 | |
| JP | 2003169794 A | 6/2003 | |
| JP | 2005052308 A | 3/2005 | |
| JP | 2006141669 A | 6/2006 | |
| JP | 2007289408 A | 11/2007 | |
| WO | 2006126108 A1 | 11/2006 | |
| WO | WO 2006126108 A1 * | 11/2006 | |

OTHER PUBLICATIONS

Patrick Perry, "The Cutting Edge: Killing Cancer with Protons," The Saturday Evening Post, (Jul./Aug. 2007), pp. 38-40.
Siemens AG. "Artis Zeego Multi-Axis System," <http://www.medical.siemens.com/webapp/wcs/stores/servlet/ProductDisplay~q_catalogId~e_-11~a_catTree~e_100010,1007660,12751,14412~a_langId~e_-11~a_productId~e_181902~a_storeId~e_10001.htm>.
EP Office Action from corresponding EP Application No. 11163283.2, dated Sep. 26, 2012.
FR Search Report and Written Opinion from FR Application No. 0953407, Feb. 2, 2010.
Unofficial English translation of Japan Office Action issued in connection with corresponding JP Application No. 2010-289716 on Sep. 2, 2014.
U.S. Appl. No. 12/638,201, filed Dec. 15, 2009, Bernard Bouvier.
Unofficial English translation of Office Action issued in connection with corresponding CN Application No. 201010604230.0 on Jan. 27, 2014.
European Office Action issued in connection with corresponding EP Application No. 11163283.2 on Sep. 1, 2015.

* cited by examiner

SYSTEM AND METHOD TO AUTOMATIC ASSIST POSITIONING OF SUBJECT IN MOBILE IMAGE ACQUISITION

RELATED APPLICATIONS

This application is a continuation in part (CIP) of and claims priority to French Application No. 0953407 entitled "X-ray machine" filed on May 22, 2009; U.S. patent application Ser. No. 12/638,201 entitled "System and Method to Automatic Assist Mobile Image Acquisition", filed on Dec. 15, 2009; and "System and Method to Automatically Assist Mobile Image Acquisition", filed on Dec. 18, 2009, all hereby incorporated herein by reference in their entirety.

BACKGROUND

The subject matter herein relates generally to image acquisition, and more specifically, to a method and arrangement to assist image acquisition of a subject. Although the foregoing description refers to medical imaging, the system is also applicable to industrial imaging.

Medical imaging systems encompass a variety of imaging modalities, such as x-ray systems, computerized tomography (CT) systems, and the like. Medical imaging systems generate images of an object, such as a patient, for example, through exposure to an energy source, such as x-rays passing through a patient. The generated images may be used for many purposes. For instance, internal defects in an object may be detected. Additionally, changes in internal structure or alignment may be determined. Fluid flow within an object may also be represented. Furthermore, the image may show the presence or absence of objects in the patient. The information gained from medical diagnostic imaging has applications in many fields, including medicine and manufacturing.

A certain conventional medical imaging system includes a mobile C-arm system. The mobile C-arm system can be used for general surgery, vascular procedures, and cardiac procedures, for example. The conventional mobile C-arm system is equipped with a radiological source or transmitter in opposed relation to a radiological detector (e.g., an image intensifier), and both are moved in relation to the imaged subject. With the subject positioned between the radiological source and detector, the C-arm system is moved and rotated so as to pass radiation through the imaged subject from various directions. As the radiation passes through the subject, anatomical structures cause variable attenuation of the radiation passing through the imaged subject and received at the detector. The detector translates the attenuated radiation into an image employed in diagnostic evaluations. In typical medical procedures around such imaging systems, multiple physicians, nurses, and technicians are located in close proximity to the imaged subject.

BRIEF SUMMARY

There is a need for a mobile imaging system that can be readily and automatically located in arbitrary positions in a crowded work environment. The above-mentioned needs are addressed by the embodiments described herein in the following description.

According to one embodiment, a method of image acquisition of a subject supported from a floor is provided. The method comprises the steps of: providing table system having a tabletop in support of the subject from the floor, and a mobile device having a drive to automatically transport the table system across the floor; identifying a current position and calculating a path relative to a reference to a pre-programmed target position for image acquisition; and communicating an instruction to the mobile device to transport the table system along the path to the pre-programmed target position.

According to another embodiment, a system to perform image acquisition of a subject supported from a floor is provided. The system comprises an imaging system operable to perform image acquisition of the subject; and a table system in mobile support of the subject from the floor, the table system including a mobile device to transport the subject across the floor.

Systems, methods, and computer program products of varying scope are described herein. In addition to the aspects and advantages described in this summary, further aspects and advantages will become apparent by reference to the drawings and with reference to the detailed description that follows.

DETAILED DESCRIPTION

In the following detailed description, reference is made to the accompanying drawings that form a part hereof, and in which is shown by way of illustration specific embodiments, which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

Figure 1:
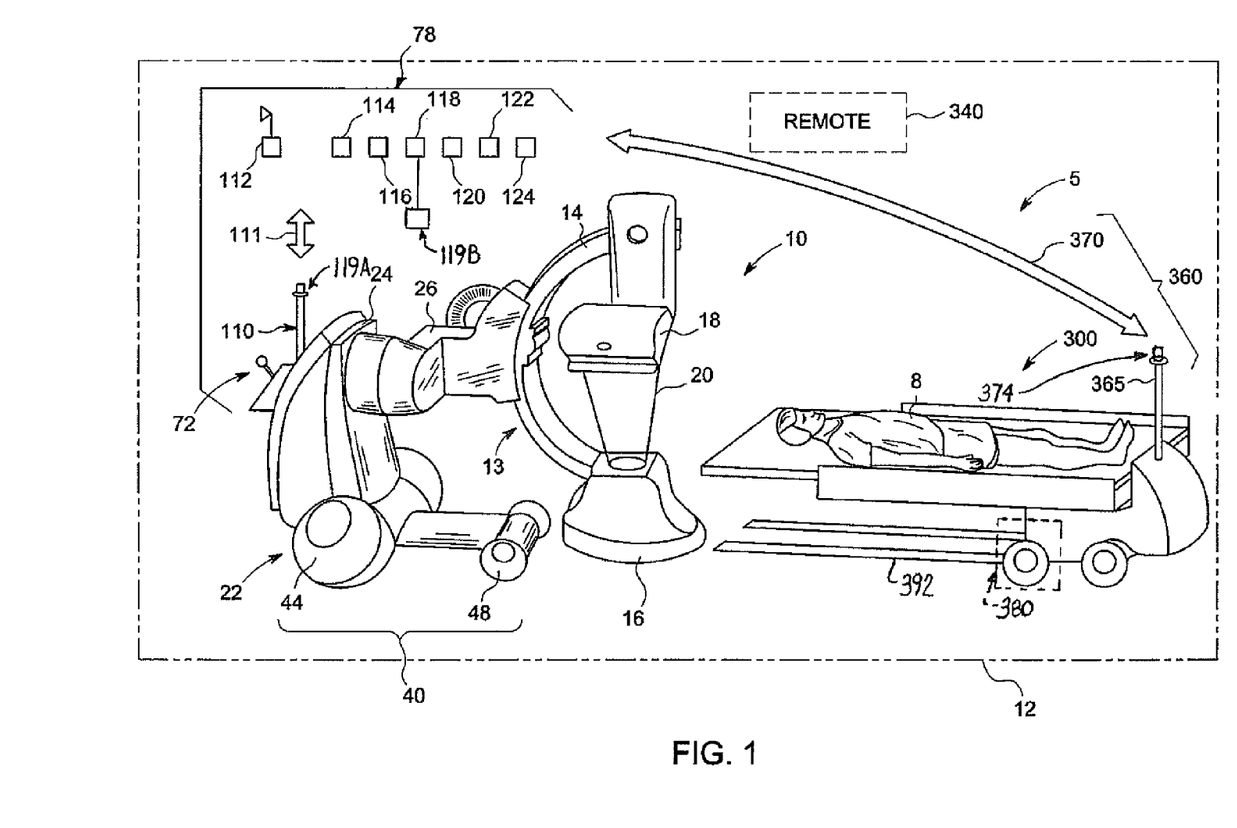
FIG. 1 shows a schematic diagram of an embodiment of a mobile imaging system of the subject matter described herein.

FIG. 1 shows an imaging system 5 to perform image acquisition of a subject or patient 8 of the subject matter described herein. An embodiment of the imaging system 5 can include an X-ray machine 10 operable to pass X-rays through the subject or patient 8 and then detect and process acquired image data for interpretation. Yet, the type of imaging system (e.g., computerized tomography (CT), ultrasound (US), electron beam tomography (EBT), magnetic resonance (MR), fluoroscopic, angiographic, positron electron emission (PET), etc.) can vary.

One embodiment of the X-ray machine 10 is a vascular type and located in an examination room or operating room or hybrid room (represented in the form of a frame referenced 12). The X-ray machine 10 can be operated remotely, for example so that an operator can be shielded from the radiation. Alternatively, the X-ray machine 10 can be placed in the examining or operating room 12 so that a health care provider can view acquired image data while performing a medical procedure on the patient 8.

The X-ray machine 10 can include a gantry 13 comprising an arm 14 that can rotate in at least two dimensions of space around the patient 8. The arm 14 can be generally C-shaped and in support of an X-ray tube 16 which is the X-ray source at one of its ends and a detector 18 at another of its ends. Yet, the shape of the arm 14 can be curvilinear, angular, circular or O-shaped, etc. and is not limiting on the subject matter described herein. Examples of the arm 14 can be C-shaped as manufactured by GENERAL ELECTRIC® Corporation, the mobile C-shaped arm as manufactured by Ziehm Imaging Incorporated, and the O-ARM® as manufactured by MEDTRONIC® Inc. The x-ray tube 16 can be generally operable to send an X-ray beam 20 along a direction of emission.

The detector 18 is hooked to the arm 14 opposite the tube 16 and in the direction of emission. The X-ray tube 16 and the image detector 18 can be mounted at the opposite ends of the arm 14 so that the X-rays emitted by the tube 16 can be incidental to and detected by the detector 18. The detector 18 can be connected to a lift (not shown) used to raise and lower the detector 18 in the direction of emission.

For example, during a radiography exposure, the x-ray tube 16 and the detector 18 can be positioned so that when, for example, the patient 8 is interposed between the X-ray tube 16 and the detector 18, and is irradiated by X-rays, the detector 18 produces data representing characteristics of the interposed patient 8 that can be conventionally displayed on a monitor (not shown) and stored electronically.

An embodiment of the arm 14 can be mounted on a mobile carriage or platform or device 22 through a support element 24. The support element 24 can be mounted fixedly on the mobile device 22. The arm 14 can be connected to the support element 22 by a rotating arm 26. The arm 14 can be mounted so as to be sliding relative to the rotating arm 26. The rotating arm 26 can rotate about an axis passing through the X-ray beam 20. This rotating assembly of the rotating arm 26 on the support element 24 can enable the X-ray tube 16 and the image detector 18 to move rotationally along or around the arc-shape of the rotating arm 26. The arm 14, the support element 24, and the rotating arm 26 can be hinged relative to one another to enable the X-ray machine 10 to move the x-ray tube 16 and detector 18 in generally three dimensions to achieve images of the internal organ of the patient 8 to be examined at different values of incidence. By combining the motion of rotation of the moving parts of the X-ray machine 10, the X-ray beam 20 can describe all the directions of sending of the X-rays included within a sphere.

Figure 2:
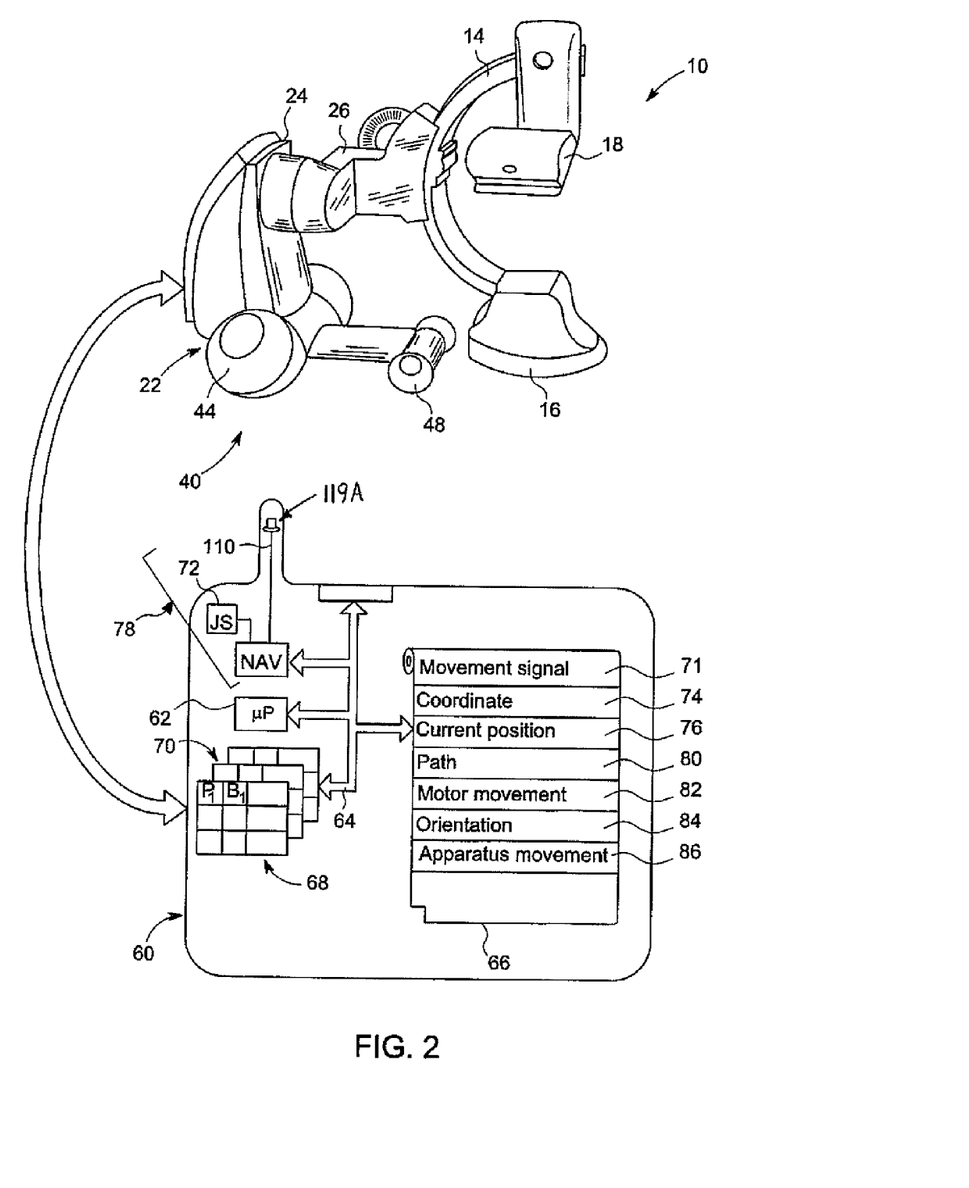
FIG. 2 shows a detailed schematic diagram of an embodiment of a brake system to selectively restrain movement of the mobile platform assembly and imaging system of FIG. 1, the brake system in a stand-by or retracted state.
Figure 3:
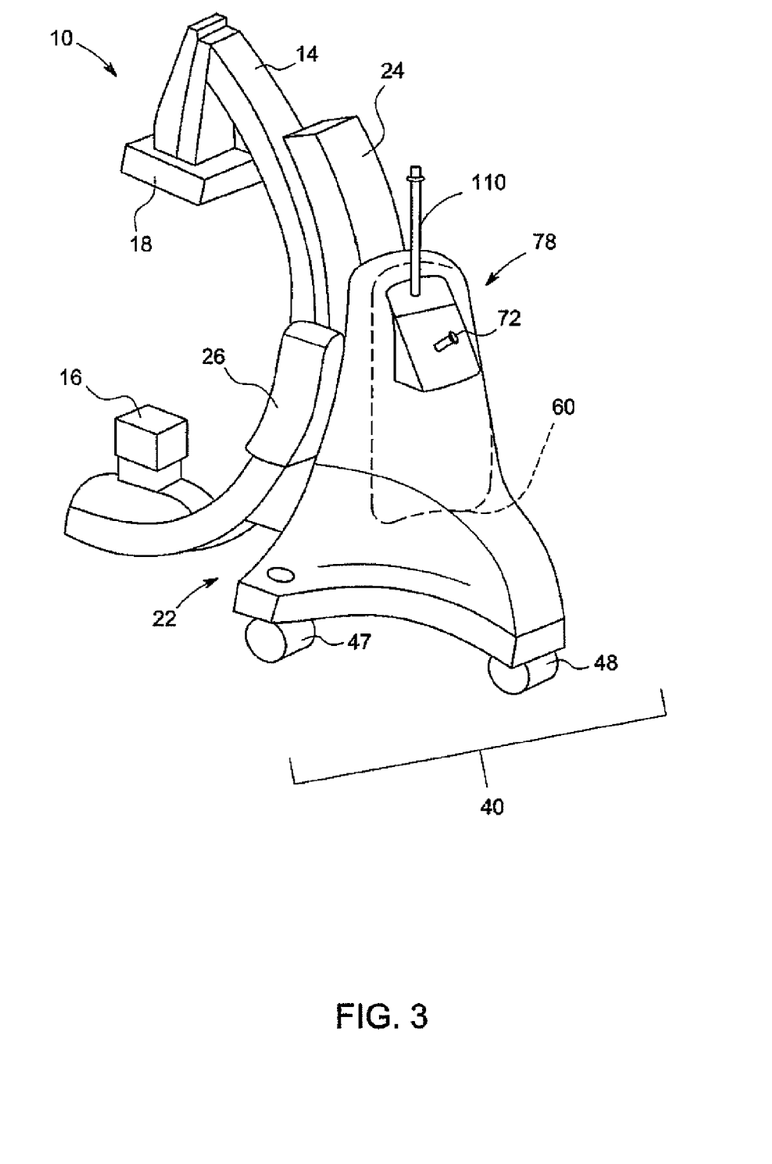
FIG. 3 shows a detailed schematic diagram of an embodiment of a brake system to selectively restrain movement of the mobile platform assembly and imaging system of FIG. 1, the brake system in restraint of movement or clamped state of the mobile device and imaging system of FIG. 1.

The embodiment of the mobile device 22 can be generally configured to move the X-ray machine 10 on the ground. An embodiment of the mobile device 18 can include a wheeled or roller system 40 operable to move or shift the mobile device 22 in every direction of the plane represented by the ground, including rotation of the mobile device 22 about a vertical axis passing through the X-ray beam 20. An embodiment of the roller system 40 comprises at least one motor driven and guide wheel 44 and at least one free wheel 48. Another example of the roller system 32 may include holonomic type wheels. The type of wheeled or roller system 32 can vary. FIG. 2 illustrates an embodiment of the mobile device 18 that includes two motor driven and guide wheels 44 placed in the rear of the mobile device 18 opposite the arm 14. FIG. 3 illustrates an embodiment of the mobile device 18 that includes two motor-driven and guide wheels 44 placed toward the front and one free wheel located toward the rear 48. The number and location of the motor driven and guide wheels 44 or free wheel(s) 48 can vary.

The mobile device 22 can also include a drive (e.g., electric, pneumatic, hydraulic, etc.) 50 operable to move the wheels 44, 48. An embodiment of the drive 50 can include a direction motor coupled to a driving motor. The connection of the wheels 44, 48 to the drive 50 can be accordingly to that known to those skilled in the art. The mobile device 22 can be electrically powered in a fashion independent of that of the X-ray machine 10.

The x-ray machine 10 can be operated in combination with an examination table or bed 34 on which the patient 8 reclines. The X-ray machine 10 can be shifted, moved or positioned in a working mode so that the examination table 34 is placed within the C-shape of the arm 14 such that the x-ray tube 16 can be located beneath the examination table 34 and the detector 18 located above the examination table 34 or vice versa and the patient 8 to be examined positioned in the path of the X-ray beam 20.

As illustrated in FIG. 2, the X-ray machine 10 can include a controller or control unit 60 to automatically control the drive 50 to move the wheels 44 of the mobile device 22. An embodiment of the control unit 60 can include a processor or microprocessor 62 connected to a bus 64, and a program memory 66 and data memories 68 and 70. The program memory 66 can be divided into several zones or modules, each module corresponding to a function or a mode of operation or action of the X-ray machine 10. An action can correspond to the implementation of one or more modules by the processor 62, connected to the program memory 66 in which the module is stored, of all or part of the instruction codes forming the module. Actions can be attributed to programs such that the actions can be executed by the processor 62, where the processor 62 can be controlled by instruction codes recorded in the program memory 66 of x-ray machine 10. These instruction codes can implement the means that the machine 10 can carry-out the action.

The discussion and illustration of the zones or memories 66, 68, 70 described herein are for example illustration of the layout of components and recordings of data. These zones or memories 66, 68, 70 can be unified or distributed according to constraints of size of the database and/or the speed of the processing operations desired.

One embodiment of the program memory 66 includes a zone 70 of instruction code to receive a movement signal corresponding to the activation of the position controls (e.g., buttons, touch-screen, toggle, joystick, etc.) 72 of the mobile device 22 or on the X-ray machine 10. The position controls 72 can also be part of a remote control unit 73.

Zone 74 can comprise instruction code to extract, from the data memory 68, the coordinates of the position to be attained by the X-ray machine 10, on the basis of the received signal described above with respect to zone 70.

The zone 76 of instruction code can be in communication with or command a navigation system 78 in order to determine the coordinates of the current position of the X-ray machine 10. The navigation system 78 can comprise manual position controls 72 to control movement of the mobile device 22 and/or the drive system of the arm 14 of the X-ray machine 10. One embodiment of the position controls 72 can control movement of the mobile device 22 in various directions (e.g., forward, backward, leftward or rightward) as well as control similar shifts to image acquisition (e.g., panoramic view, horizontal, vertical and zooming). The navigation system 78 can be operable to convert a shift or movement of the position controls 72 into electrical signals that can be interpreted by the control unit 60 of the mobile device 22. The joystick 79 can thus control movement of the mobile device 22 in a pre-programmed trajectory desired by the operator.

Zone 80 can comprise instruction code to command the navigation system 78 in order to establish a path of movement, from the current position and from the position to be attained of the x-ray machine 10.

Zone 82 can comprise instruction code to command operation, activation, working, or movement of the drive 50.

Zone 84 can comprise instruction code to receive a work orientation signal for the arm 14 of the X-ray machine 10 corresponding to the actuation of the orientation commands for image acquisition of the patient 8. These orientation and position commands can be distinct.

Zone 86 can comprise instruction code to command movement of the X-ray machine 10 moving parts, including the arm 14, the rotating arm 26, the support element 15 and/or the roller system 40. The movement of these parts 14, 24, 26, 40, as a function of the orientation signal, can be done such that the region of interest of the patient 8 to be imaged remains positioned within the X-ray beam 20.

An embodiment of the data memory 68, 70 can include predetermined parking and working positions. A parking position can be a place or location where the X-ray machine 10 can be positioned when in parking or idle mode outside a restricted space needed for a medical procedure. A working position can be a place or location where the X-ray machine 10 to perform image acquisition of the patient 8. One example of the data memory 68, 70 can be structured in a table format of rows and columns, where each row corresponds to the coordinates of a position of the X-ray machine 10 and each column corresponds to a piece of information on this position of the X-ray machine 10. For example, a row can correspond to the coordinates of a predetermined working position or parking position of the X-ray machine 10 and a column can correspond to a shift signal associated with the actuation of a given positional command of the X-ray machine 10.

The data memory 68, 70 can also include predetermined working orientations for the moving parts 14, 24, 26 of the X-ray machine 10 or the roller system 40. A working orientation can be a configuration of the X-ray machine 10 where the arm 14, the support element 24, the rotating arm 26, and the roller system 40 can shift or move into a radiography position according to the orientation signal. This shift may not affect the position of the region of interest of the patient 8 to be examined relative to the X-ray beam 20.

An embodiment of the data memory 68, 70 can be structured in a table format of rows and columns, where each row corresponds to a working orientation of the moving parts 14, 24, 26 or 40 of the X-ray machine 10 and each column corresponds to a piece of information on this orientation. For example, rows can correspond to the movements to be made by each moving part 14, 24, 26, or 40 and columns can correspond to movement signals associated with the actuation of a given orientation command of the X-ray machine 10. The positional and orientation command may be actuated simultaneously or consecutively.

Figure 4:
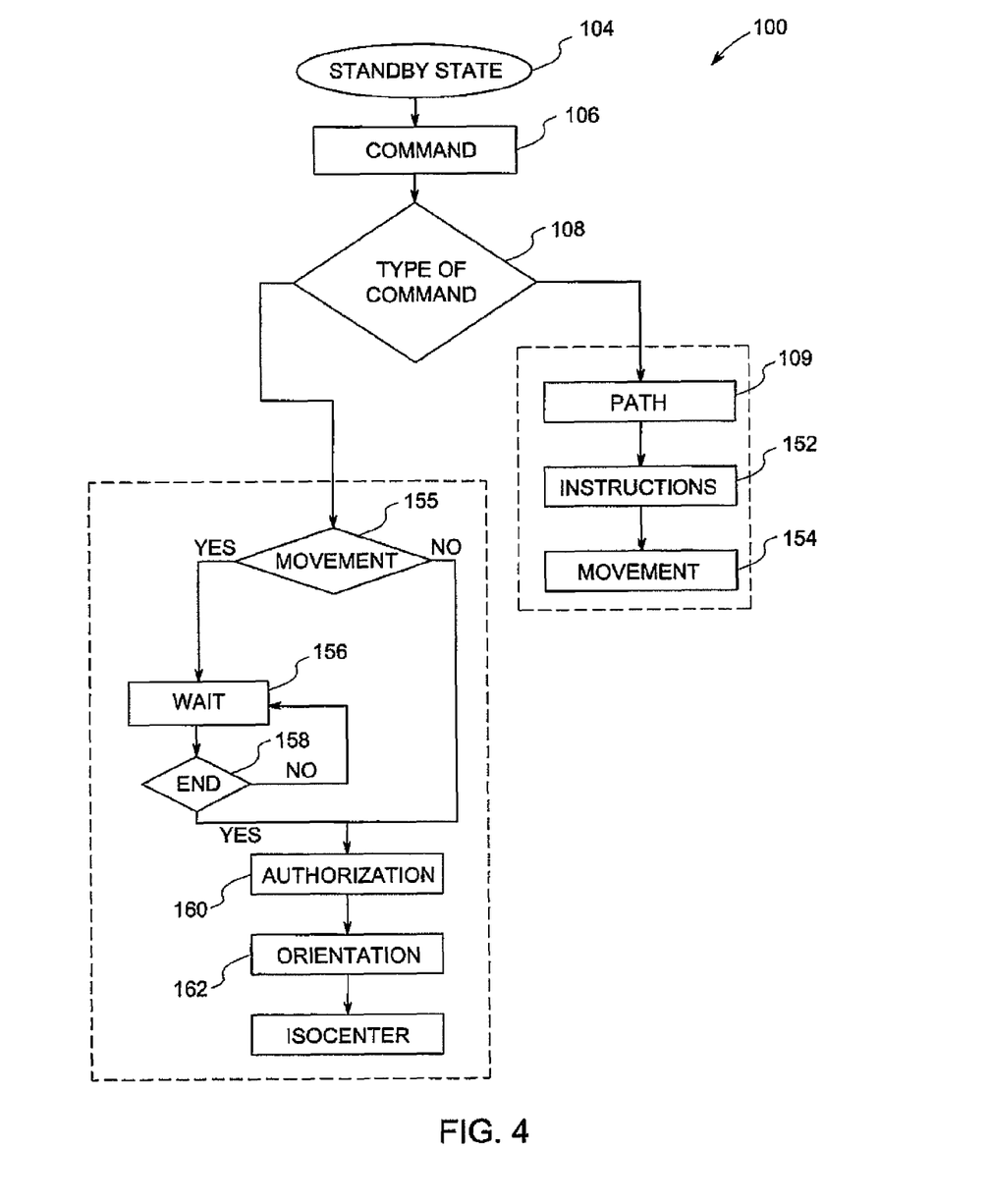
FIG. 4 shows a schematic flow diagram of an embodiment of a method of navigating the mobile device in combination with the imaging system of FIG. 1.

FIG. 4 shows an embodiment of a method 100 of the subject matter herein. A first preliminary step 104 can include putting the X-ray machine 10 in a standby mode. Step 106 can include receiving a positional or orientation command of the X-ray machine 10.

Step 108 can include identifying the type of acquired signal (e.g., positioning signal). Step 109 can include computing a path to place the X-ray machine 10 in the desired position per the received positional signal in step 106. To achieve this end, the control unit 60 can activate the navigation system to: compute the current position of the X-ray machine 10; compute an optimum or pre-programmed trajectory between the current position and the coordinates contained in the positional signal received in step 106; and guide movement of the X-ray machine 10 by reference to this path.

In one embodiment, the navigation system 78 can include a wireless communication or tracking system (e.g., including an antenna, transceiver, receiver, emitter or transmitter or combination thereof) 110 in wireless communication or link (e.g., global satellite positioning (GPS), radiofrequency, infrared, optical recognition of bar codes or shapes, ultrasound, electromagnetism, etc.) 111 with various stationary receivers or transmitters having either a unique identification code or positional coordinate. The stationary receivers or transmitters may be positioned at a height and/or on the ground and/or on the ceiling or on the table 34.

For example, the navigation system 78 can include wireless tags (e.g., electromagnetic, radio frequency, ultrasonic, infrared, optical, etc.) 112 provided with a battery that gives them the energy needed to transmit a low frequency, medium frequency or high frequency signal over a distance (e.g., from one centimeter to a few centimeters). Wireless tags 112 may be autonomous from an energy point of view to activate in response to a variable electromagnetic or radiofrequency signal.

The navigation system 78 can be generally operable to exchange or compute position coordinates of the X-ray machine 10 relative to predefined path or trajectory. On the basis of the position coordinates, the navigation system 78 can compute a current position and compute a trajectory or path or correction thereof relative to the predefined trajectory.

One example of the navigation system 78 can include optical readers operable to read or decode barcodes (e.g., two-dimensional) 114 representative of two-dimensional coordinates of their position in the environment (e.g., on the ground of the room 12 and/or on the ceiling or on the table 34) of the X-ray machine 10. The navigation system 78 can include an optical reader designed to decode the information contained in the barcodes. The optical reader can be placed beneath the mobile device 22 facing the ground and/or above the mobile device 22 facing the ceiling or in any variant facing direction therebetween so as to detect and read the bar code. From the coordinates of the position of the barcode 114, the navigation system 78 can compute the current position and compute a trajectory and corrects the trajectory of the X-ray machine 10 or mobile device 22 relative to a preliminarily computed or pre-programmed trajectory.

In another embodiment, the navigation system 78 can be in communication with a GPS or global positioning system 116 so as to be operable to compute the current position of the X-ray machine 10, its trajectory or path, or its the pre-programmed trajectory.

Another example of the navigation system 78 can include a system 118 of optical or laser emitter 119A and/or reflectors or detectors 119B operable to perform general real-time tracking of position and updated path or trajectory or correction thereof to locate X-ray machine 10 supported on the mobile device 22. The system 118 of laser emitters 119A and/or reflectors or detectors 119B can be located at one or stationary locations in communication with the navigation system 78 of the X-ray machine 10 or mobile device 22. In response to receiving a positioning signal according to a predefined trajectory or manual input, the navigation system 78 can activate emission of a laser beam from the system 118 and measure the duration between the incident laser beam and the reflected laser beam between the laser emitter 119A and/or reflector or detectors 119B. Based on the measured duration, the navigation system 78 can compute the current position of the X-ray machine 10 or mobile device 22 relative to an optimal or pre-programmed trajectory, and can generate signals to steer the mobile device 22 relative to the optimal or preprogrammed trajectory or path, and adjustments thereto accordingly. According to one embodiment of the system 118, the laser emitter 119A can be mounted on the mobile device 22 or system 5. The laser emitting antenna 119A can rotate in emitting the laser beam, and the system 118 can measure the distance between the system 5 and one or more the reflectors or deflectors 119B stationed at the walls of the room 12. The system 118 can also measure an angle of incident beam or reflected laser beam or the laser reflector or deflector 119B relative to a reference (e.g., absolute zero can be defined by horizontal or vertical in an x-y-z coordinate or polar coordinate system calibrated to the system 118) of the system 118.

In another embodiment, the navigation system 78 can include an electromagnetic field link 120 to define the path or trajectory of the X-ray machine 10 or mobile device 22. The navigation system 78 can detect the position of the X-ray machine 10 and/or mobile device 22 dependent on the electromagnetic filed link 120 to steer the path or trajectory of the X-ray machine 10 and/or mobile device 22 relative to a pre-computed or pre-programmed trajectory or path.

In another embodiment, the navigation system 78 can include an optical guidance system 122 having longitudinal markings that constitute a reference for the trajectory of the X-ray machine 10 and/or mobile device 22. The optical guidance system 122 can include a camera or similar device at the forward part of the mobile device 22 to form an image of the path of the mobile device 22 or X-ray machine 10. Depending on the data communicated from the optical guidance system 122 to the control unit 60, the control unit 60 can compute the position of the X-ray machine 10 and/or mobile device 22 and correct the trajectory or path relative to a pre-computed or pre-programmed trajectory.

Another embodiment of the optical guidance system 122 can include at least one camera in communication with the X-ray machine 10 and/or mobile device 22 from a stationary position in the room 12. The control unit 60 can be operable to process acquired data from the optical guidance system 122 and compute an environment or landscape with a predetermined vicinity or threshold of the X-ray machine 10 and/or mobile device 22, including detection of potential obstacles. The control unit 60 can compute the position or location of the X-ray machine 10 and/or mobile device 22 and correct its trajectory relative to a pre-computed or pre-programmed trajectory.

In another embodiment, the navigation system 78 can include sensors (e.g., accelerometers) 124 capable of measuring a direction and/or magnitude of shift or movement) of the X-ray machine 10 and/or roller system 40 of the mobile device 22. Based on these acquired measurements, the control unit 60 can use odometry techniques to compute the position of the X-ray machine 10 and/or mobile device 22. Starting from a known initial position and computing the measured movements, the control unit 60 can compute the current position of the X-ray machine 10 and/or mobile device 22. Depending on the result of this computation, the control unit 60 can correct the trajectory or path of the X-ray machine 10 and/or mobile device 22 relative to a trajectory a pre-computed or pre-programmed trajectory.

In another embodiment, the data memory 68, 70 can include information on a mapping of the environment of the X-ray machine 10, the mapping including reference coordinates of a predefined parking position of the X-ray machine 10.

Figure 5:
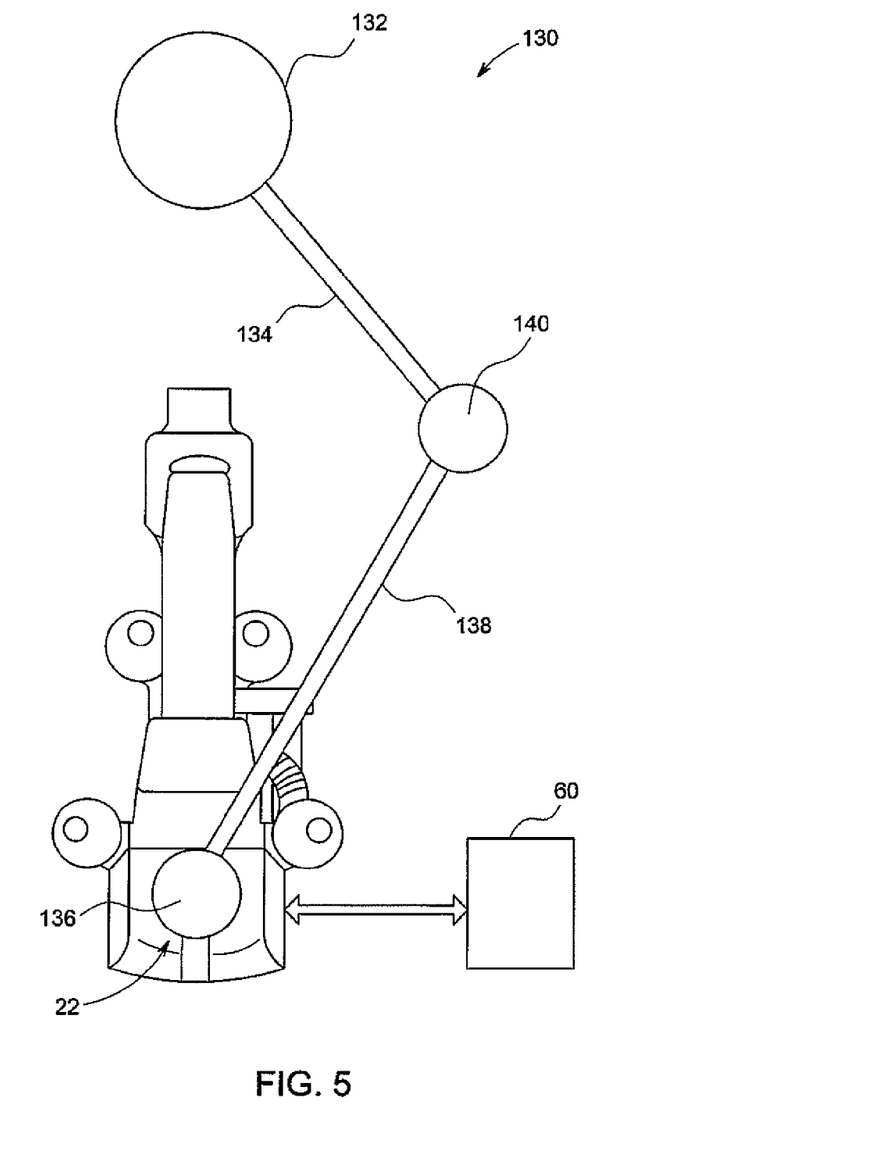
FIG. 5 shows a flow diagram of an embodiment of the mobile carriage system of FIG. 1 in management of transport and restraint of the imaging system of FIG. 1.

FIG. 5 describes another embodiment of the mobile device 22 of the X-ray machine 10 connected by a mechanical linkage 130 to a stationary platform (e.g., the ceiling or to the walls of the room 12) 132. One example of the mechanical linkage 130 can include a first arm 134 connected by a first hinge device 136 to the mobile device 22. This first arm 134 can be connected to a second arm 138 by a second hinge device 140. The number of arms and hinges can vary. This second arm 138 can be coupled 10 the hinge device 132 at the mobile device 22. The mechanical linkage 130 of hinged arms 134, 138 can include encoders (not shown) operable to convert detected mechanical movement of the arms 134, 138 into a numerical variable and communicate to the control unit 60, and the control unit 60 can combine the tracked angular position of the different encoders to guide or steer movement of the mobile device 22.

One or more of the above embodiments of the navigation system 78 or components thereof may be combined with others to refine the computation precision. The type of navigation system 78 can vary.

Step 150 can include communicating movement instructions to the drive of the mobile device 22. Step 152 can include controlling steering or guiding movement of the drive of the mobile device 22 through the pre-determined trajectory. The control unit 60 can steer or guide movement of the X-ray machine 10 via the mobile device 22 from a starting point to a position controlled by determining the position, the trajectory or pre-programmed trajectory, corrected if necessary, and cause corrections or changes in guidance with reference to this trajectory.

If the control unit 60 detects in step 108 that the type of received command signal is a navigation or an orientation signal, the control unit 60 can execute the following. Before processing the received orientation signal, step 155 can include computing if one or more of the above steps are being executed. If this is the case, step 156 can include storing or causing the navigation or orientation signal to sit idle without further processing. Step 158 can include computing a check as to whether the execution of one or more of the above steps is terminated in order to authorize the processing of the navigation or orientation signal. If no detection of execution of one or more of the above steps, step 160 includes authorizing further processing of this navigation or orientation signal.

Step 162 can include causing movement of the navigation or orientation of one or more of the arm 13, the support element 24, the rotating arm 26 and/or the roller system 40 to correspond to instruction in the navigation or orientation signal so as to position the X-ray beam 20 in a desired direction to perform image acquisition of the desired region of interest of the patient 8.

In the event of receiving a new orientation command, the control unit 60 can steer movement of the arm 14, the support element 24, the rotating arm 26, and/or the roller system 40 in a controlled manner and at a desired navigation or orientation while at the same time keeping X-ray beam 20 in the region of interest to be examined.

A technical effect of the subject matter described herein is to enhance changes in image acquisition with changes to the region of interest to be examined by moving the X-ray machine 10 via the roller system 40 of the robotic mobile device 22 from one working position to another.

Figure 6:
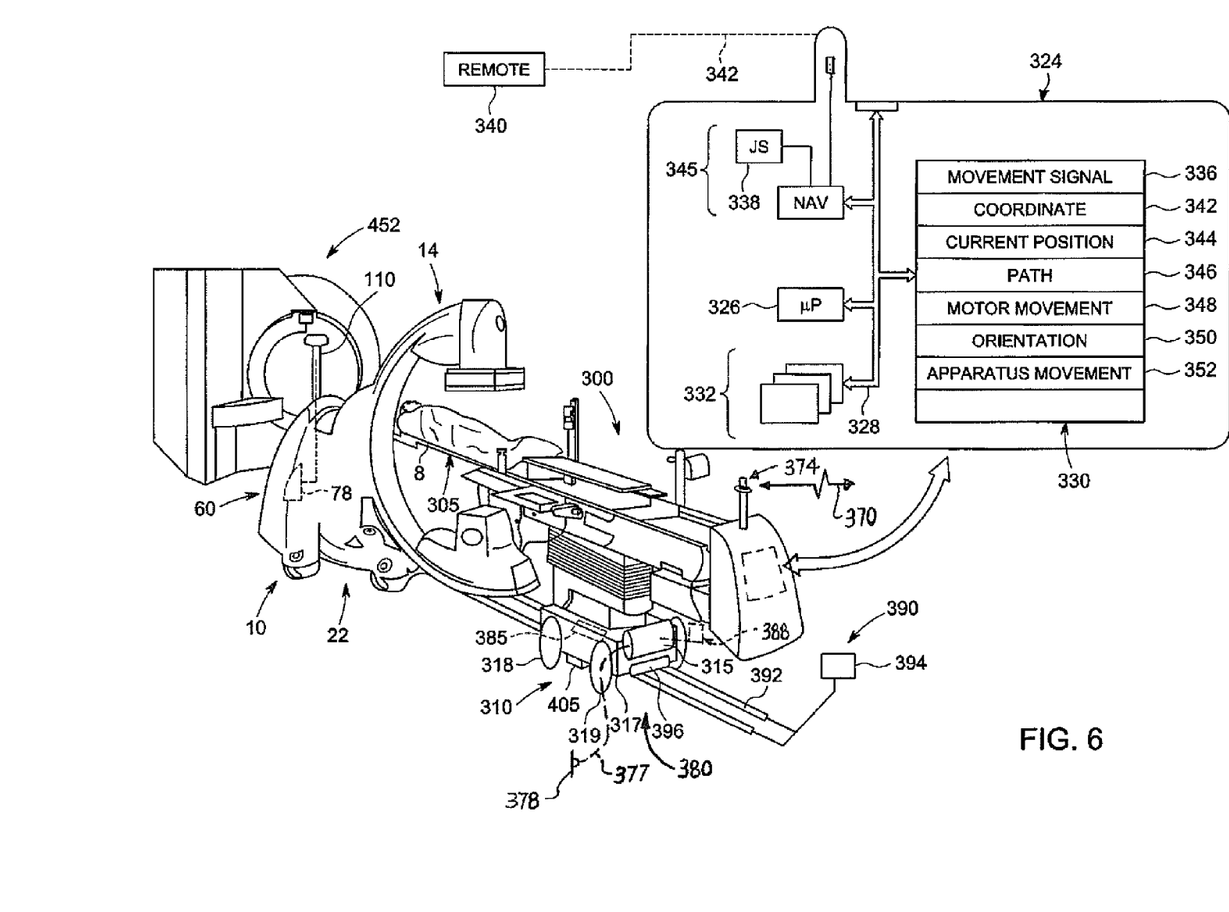
FIG. 6 illustrates an embodiment of a table system supported a mobile device in transport of a subject between a first imaging system on a second mobile device and a third imaging system.

FIG. 6 illustrates a schematic diagram of a robotically operated subject support or table system 300. One embodiment of the table system 300 can be configured to support the subject 8 in image acquisition by the imaging system 5. One embodiment of the table system 300 can be in support of the subject 8 during a surgical or vascular medical procedure. Yet, the application or type of use of the table system 300 can vary.

An embodiment of the table system 300 can include a tabletop 305 supported on a mobile device 310 having a drive or motor 315 (e.g., electrical-driven, hydraulic, etc.) to drive movement of a wheel platform or carriage 317 in support of the tabletop 305. The wheel carriage 317 can be operable to move or shift the mobile device 310 in every direction of the plane represented by the ground, including rotation of the mobile device 310 about a vertical axis extending through the mobile device 310.

An embodiment of the wheel carriage 317 can comprise at least one guide wheel 318 and at least one motor driven wheel 319, similar to the roller system 40 described above. The at least one or more guide wheels can be operable to rotate in through a three-sixty degree range around a generally vertical axis. The at least one guide wheel can rotate freely or actuate (e.g., mechanical, electrical-driven, hydraulic driven) in a controlled manner. The at least one or more motor driven wheels 319 can mechanically interlinked with and to be driven by the drive or motor 315. The type of wheels (e.g., holonomic, roller, etc.), as well as the number and location of the wheels can vary.

The table system 300 can include a controller or control unit 324 to automatically control the drive or motor 315 to move the wheels 318, 319 of the mobile device 310, similar to the control unit 60 described above. An embodiment of the control unit 324 can include a processor or microprocessor 326 connected to a bus 328, and a program memory 330 and data memories 332. The program memory 330 can be divided into several zones or modules, each module corresponding to a function or a mode of operation or action of the table system 300. An action can correspond to the implementation of one or more modules by the processor 326, connected to the program memory 330 in which the module is stored, of all or part of the instruction codes forming the module. Actions can be attributed to programs such that the actions can be executed by the processor 326, where the processor 326 can be controlled by instruction codes recorded in the program memory 330 of the table system 300. These instruction codes can implement the means that the table system 300 can carry-out the action.

The discussion and illustration of the zones or memories 330, 332 described herein are for example illustration of the layout of components and recordings of data. These zones or memories 330, 332 can be unified or distributed according to constraints of size of the database and/or the speed of the processing operations desired.

One embodiment of the program memory 330 includes a zone 336 of instruction code to receive a movement signal corresponding to the activation of the position controls (e.g., buttons, touch-screen, toggle, joystick, etc.) 338 of the mobile device 310 or on the table system 300. The position controls 338 can also be part of a remote control unit 340.

Zone 342 can comprise instruction code to extract, from the data memory 332 the coordinates of the position to be attained by the table system 300, on the basis of the received signal described above with respect to zone 336.

The zone 344 of instruction code can be in communication with or command a navigation system 345 in order to determine the coordinates of the current position of the table system 300. The navigation system 345 can comprise the manual position controls 338 to control movement of the mobile device 310. One embodiment of the position controls 338 can control movement of the mobile device 310 in various directions (e.g., forward, backward, leftward or rightward) as well as control similar shifts to image acquisition (e.g., panoramic view, horizontal, vertical and zooming). The navigation system 345 can be operable to convert a shift or movement of the position controls 338 into electrical signals that can be interpreted by the control unit 324 of the mobile device 310. The position controls 338 can thus control movement of the mobile device 310 in a pre-programmed trajectory desired by the operator.

Zone 346 can comprise instruction code to command a navigation system 345 in order to establish a path of movement, from the current position and from the position to be attained of the table system 300.

Zone 348 can comprise instruction code to command operation, activation, working, or movement of the drive or motor 315 of the table system 300.

Zone 350 can comprise instruction code to receive a work orientation signal for the tabletop 305 of the table system 300 corresponding to the actuation of the orientation commands of the X-ray machine 10 for image acquisition of the patient 8. These orientation and position commands can be distinct.

Zone 352 can comprise instruction code to command movement of the table system 300 moving parts, including the tabletop 305 and/or the mobile device 310. The movement of these parts 305 and 310 as a function of the orientation signal can be done such that the region of interest of the patient 8 to be imaged remains positioned for image acquisition by the X-ray machine 10.

An embodiment of the data memory 332 can include predetermined parking and working positions of the table system 300. A parking position can be a place or location where the table system 300 can be positioned when in parking or idle mode outside a restricted space needed for a medical procedure. A working position can be a place or location for the table system 300 to perform image acquisition of the patient 8. One example of the data memory 332 can be structured in a tabular format of rows and columns, where each row corresponds to the coordinates of a position of the table system 300 and each column corresponds to a piece of information on this position of the table system 300. For example, a row can correspond to the coordinates of a predetermined working position or parking position of the table system 300 and a column can correspond to a shift signal associated with the actuation of a given positional command (horizontal or vertical angle, height, etc.) of the tabletop 305 of the table system 300.

The data memory 332 can also include predetermined working orientations for the moving parts tabletop 305 and mobile device 310 of the table system 300 in combination with a working orientation of the X-ray machine 10. For example, the arm 14, the support element 24, the rotating arm 26, and the roller system 40 of the imaging system 5 or X-ray machine 10 or mobile device 22 can shift or move in generally simultaneous time frame or in according to a sequence of position events or milestones relative to the tabletop 305 or mobile device 310 of the table system 300 for image acquisition, and can be according to the orientation signal. This shift may not affect the position of the region of interest of the subject 8 to be examined.

An embodiment of the data memory 332 can be structured in a table format of rows and columns, where each row corresponds to a working orientation of the moving parts 305 and 310 of the table system 300 and each column corresponds to a piece of information on this orientation. For example, rows can correspond to the movements to be made by each moving part 305 and columns can correspond to movement signals associated with the actuation of a given orientation command of the table system 300. The positional and orientation commands may be actuated simultaneously or consecutively.

An embodiment of the navigation system 345 can include automated-guided vehicle technology and be wireless powered, similar to the imaging system 5 or X-ray machine 10 described above, to instruct the mobile device 310 to automatically move the wheel carriage in support of the table system 300 to a position for a desired distance/direction or to a desired position in predefined path, without waiting for user input instructions between changes in direction or speed or position. The wireless navigation system and wireless powered capability of the mobile device 310 can remove the extension of clusters of power cables, hydraulic lines, data transfer cables, etc. that can become entangled, create interference, inhibit movement or access, or increase a likelihood of a tripping hazard, etc. with movement of the robotic table system 300 in transport between positions or locations of a medical procedure or image acquisition.

An embodiment of the navigation system 345 can include a wireless tracking system 360 (e.g., global satellite positioning (GPS), radiofrequency, infrared, optical recognition of bar codes or shapes, ultrasound, electromagnetism, etc.). An embodiment of the wireless tracking system 360 can include transceiver, receiver, transmitter/receiver or antenna 365 or combination thereof in communication via a wireless link 370, similar to the wireless communication or tracking system 110 described above. At least a portion of the navigation system 345 can be integrated or combined or part of the navigation system 78 described above, or the navigation systems 78 and 350 can be independent of one another. The tracking system 360 may be positioned at a height and/or on the ground and/or on the ceiling or on the tabletop 305.

In another example, the navigation system 345 can include the wireless tags (e.g., electromagnetic, radio frequency, ultrasonic, infrared, optical, etc.) 112 described above, provided with a battery that gives them the energy needed to transmit a low frequency, medium frequency or high frequency signal over a distance (e.g., from one centimeter to a few centimeters).

Another example, of the navigation system 345 can be generally operable to exchange or compute position coordinates of the table system 300 relative to predefined path or trajectory and may be in relation or correspond to the path or trajectory of the imaging system 5 or X-ray machine 10 described above. On the basis of the position coordinates, the navigation system 345 can compute a current position and compute a trajectory or path or correction thereof relative to the predefined trajectory.

Yet another example of the navigation system 345 can include the optical readers operable to read or decode barcodes (e.g., two-dimensional) 114 representative of two-dimensional coordinates of their position in the environment (e.g., on the ground of the room 12 and/or on the ceiling or on the tabletop 305) of the table system 300. The navigation system 345 can include an optical reader designed to decode the information contained in the barcodes. The optical reader can be placed beneath the mobile device 310 facing the ground and/or above the mobile device 310 facing the ceiling or in any variant facing direction therebetween so as to detect and read the bar code. From the coordinates of the position of the barcode 114, the navigation system 345 can compute the current position and compute a trajectory and corrects the trajectory of the table system 300 or mobile device 310 relative to a preliminarily computed or pre-programmed trajectory, similar to the navigation system 78 described above.

In yet another example, the navigation system 345 can be in communication with the GPS or global positioning system 116 so as to be operable to compute the current position, trajectory or path, or the pre-programmed trajectory of the table system 300.

In yet another example, the navigation system 345 can be in communication with and/or include the system 118 of optical or laser emitter and/or reflectors or detectors 119A, 119B operable to perform general real-time tracking of position and updated path or trajectory or correction thereof to locate the table system 300 supported on the mobile device 310. The navigation system 345 can include stationary emitter or reflectors or detectors or combination thereof 119B located at one or stationary locations in communication with a laser emitter or reflector or detector 374 or combination thereof located at the table system 300 or mobile device 310. In response to receiving a positioning signal according to a predefined trajectory or manual input, the navigation system 345 can activate the emission of a laser beam and measurement the duration between the incident laser beam and the reflected laser beam. Based on the measured duration and angle of incidence or reflection of the laser beam relative to a reference (e.g., absolute zero can be defined by horizontal or vertical of an x-y-z coordinate system or polar system) of the navigation system 345, the navigation system 345 can compute the current position of the table system 300 or mobile device 310 relative to an optimal or pre-programmed trajectory, and can generate signals to steer the mobile device 310 relative to the optimal or preprogrammed trajectory or path, and adjustments thereto accordingly. An embodiment of the laser emitter, reflector or deflector or combination thereof 374 mounted on the mobile device 310 or table system 300 can be in communication with or part of the system 118 of the mobile device 22 of the imaging system 5 described above, or independent thereof. The laser emitter 374 can rotate and measure the distance between the imaging system 5 and one or more the reflectors stationed at the walls of the room 12.

Yet another example of the navigation system 345 can include the electromagnetic field link 120 to define the path or trajectory of the table system 300 or mobile device 310. The navigation system 345 can detect the position of the table system 300 or mobile device 310 dependent on the electromagnetic filed link 120 to steer the path or trajectory of the table system 300 or mobile device 310 relative to a pre-computed or pre-programmed trajectory or path.

Yet another example of the navigation system 345 can include the optical guidance system 122 having longitudinal markings that constitute a reference for the trajectory of the table system 300 and/or mobile device 310, similar to the mobile device 22 of the imaging system 5 described above. Depending on the data communicated from the optical guidance system 122 to the control unit 324, the control unit 324 can compute the position of the table system 300 and/or mobile device 310 and correct the trajectory or path relative to a pre-computed or pre-programmed trajectory.

Another embodiment of the optical guidance system 122 can include at least one camera in communication with the table system 300 and/or mobile device 310 from the stationary position in the room 12. The control unit 324 can be operable to process acquired data from the optical guidance system 122 and compute an environment or landscape with a predetermined vicinity or threshold of the table system 300 and/or mobile device 310, including detection of potential obstacles. The control unit 324 can compute the position or location of the table system 300 and/or mobile device 310 and correct its trajectory relative to a pre-computed or pre-programmed trajectory.

In another example, the navigation system 345 can include the sensors (e.g., accelerometers) 124 capable of measuring a direction and/or magnitude of shift or movement) of the table system 300 or the mobile device 310. Based on these acquired measurements, the control unit 324 can use odometry techniques to compute the position of the table system 300 or mobile device 310. Starting from a known initial position and computing the measured movements, the control unit 324 can compute the current position of the table system 300 or mobile device 310. Depending on the result of this computation, the control unit 324 can correct the trajectory or path of the table system 300 or mobile device 310 relative to a trajectory a pre-computed or pre-programmed trajectory.

According to one embodiment, a portion of the navigation system 78 of the imaging system 5 or X-ray machine 10 can be integrated with the navigation system 345 of the table system 300 or mobile device 310. The portion of the navigation systems 78 and 350 integrated with one another versus independent of one another can vary.

One embodiment of the drive or motor 315 of the mobile device 310 can be powered from a hard connection of an electrical power supply cord 377 (shown in dashed line) to a stationary electrical connector 778 (e.g., wall socket or data connector) in the room 12. Yet, the table system 300 may not include a hardwire connection to receive electrical power from a stationary electrical connector 378 (e.g., electrical wall socket) of the room 12.

Another embodiment of the drive or motor 315 of the mobile device 310 can be electrically powered directly or indirectly from a wireless power system 380 (referenced in dashed line in FIG. 1 and reference with an arrow in FIG. 6). One embodiment of the wireless power system 380 can include a battery 385 at the mobile device 310 that provides electrical power to drive the mobile device 310 to move the robotic table system 300. The battery 385 can be a rechargeable battery (e.g., lithium-ion, nickel, etc.). Another embodiment of the wireless power system 380 can include a plurality of solar cells or panels 388 (shown in dashed line) located to move with and in electrical connection to provide power to the drive or motor 315 of the table system 300.

Another embodiment of the wireless power system 380 can include an inductive power system 390 that can be independent of or in combination with the battery 385 and or solar cells or panel 388 (shown in dashed line). An embodiment of the inductive power system 390 can include an inductive transmitter (e.g., rail, bus, etc.) 392 embedded in the floor or attached at the floor in electrical communication with a power supply (e.g., AC, DC) 394 remotely located independent from the mobile device 310. The inductive transmitter 392 can be in wireless communication (e.g., magnetic, electromagnetic, etc.) across an air gap with an inductive receiver 396 attached at the mobile device 310. For example, a moving magnetic field transmitted from the inductive transmitter 392 of the wireless power system 380 across the air gap can create or generate an electrical current at the inductive receiver (e.g., stator coil) 396 located at the mobile device 310 to provide the electrical power to drive the mobile device 310. Yet, the type of wireless power system 380 can vary.

Having generally provided the above-description of a construction of the embodiment the table system 300 having a mobile device 310 of the subject matter described herein, the following is a general description of a method 400 (See FIG. 10) of operation of the table system 300. It should also be understood that the sequence or succession of the acts or steps of the method 400 as described in the foregoing description can vary. Also, it should be understood that the method 400 may not require each act or step in the foregoing description, or may include additional acts or steps not disclosed herein. One or more of following steps and acts of the method 400 can also be in the form of a computer program product having modules or zones or computer-readable program instructions that can be stored in the data memory 332 for execution by the processor 326 of the table system 300.

Assume for sake of example that the imaging system 5 or X-ray machine 10 and the table system 300 are both located in a parked or stored position, and that at least one of the imaging system 5 or X-ray machine 10 and the table system 300 can be robotically operated and remotely or wireless controlled from the remote unit 340. Although not required, the table system 300 can include an automatic brake system 405 that may also be energized to restrain movement of the table system 300 from the restrained position, as described in U.S. patent application Ser. No. 12/638,201 entitled "System and Method to Automatic Assist Mobile Image Acquisition", filed on Dec. 15, 2009; and "System and Method to Automatically Assist Mobile Image Acquisition", filed on Dec. 18, 2009, both hereby incorporated herein by reference in their entirety. Also assume that instructions to perform one or more of the following steps can be received via wireless communication from the remote unit 340.

Figure 7:
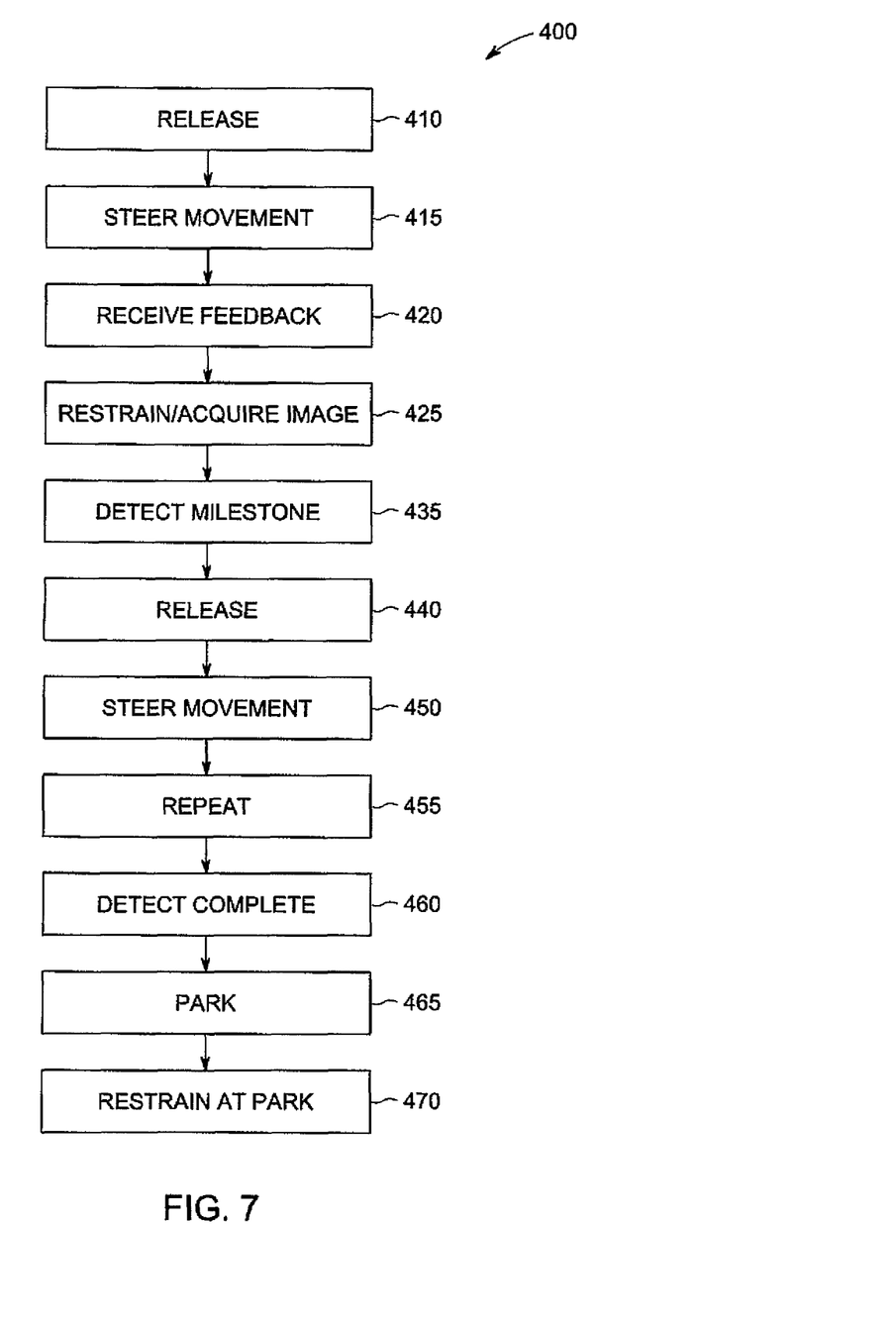
FIG. 7 illustrates an embodiment a flow diagram in management of transport of a subject in relation to a mobile image acquisition system in accordance with the subject matter described herein.

Referring to FIG. 7, step 410 can include releasing restrain of movement of the table system 300 and the imaging system 5 or X-ray machine 10. Step 415 can include instructing or communicating to the mobile device 310 to steer movement of the table system 300 to a desired position with respect to the X-ray machine 10 for image acquisition of the subject 8. An embodiment of step 415 can include communicating instructions for the mobile device 310 to steer the table system 300 to predefined locations and alignments according to a pre-defined type and/or body area and/or protocol of image acquisition to perform image acquisition on the subject 8. Also, the mobile device 350 can receive manual instructions (e.g., via joystick) to selectively supplement movement of the mobile device 310 to the desired location. Step 415 can include controlling steering or guiding movement of the drive of the mobile device 310 through the pre-determined path or to a predefined position. Step 415 can include coordinating communication of instructions to steer or guide movement of the table system 300 in combination and in sequence with automatic steering and guidance of movement the mobile device 22 or the imaging system 5 or X-ray machine 10 from a starting point to a preprogrammed position, pre-programmed trajectory or path, corrected if necessary based on current position or path, and cause corrections or changes in guidance with reference to this trajectory or path. Step 415 can further include coordinating communication of instructions to steer or guide movement of the tabletop 305 relative to the floor or remainder of the table system 300 to position the subject 8 in a pre-programmed relation or position relative to the imaging system 5 or X-ray machine 10 for image acquisition.

Step 420 can include receiving feedback that the tabletop 305 and the mobile device 310 or the table system 300 are located at the desired alignment and location with respect to the mobile device 22 or the imaging system 5 or X-ray machine 10 to perform image acquisition of the subject 8 supported on the table system 300. Step 425 can include applying a restraint force (e.g., force applied by the braking system 405) to hinder vibration or movement of the mobile device 310 or table system 300. An embodiment of the restraint force can resist vibration or tilting of the tabletop 305 of the table system 300 while performing image acquisition. Step 435 can include detecting completion or other milestone event of image acquisition at the present or pre-programmed location of the table system 300.

Step 440 can include releasing or interrupting restraint of the table system 300 (e.g., interrupt brake force applied by braking system 405). Step 450 can include automatically steering or guiding the mobile device 310 along a pre-programmed path or trajectory to move the subject 8 to another position for image acquisition. One embodiment of the step 450 includes moving the subject 8 to a second position for image acquisition by the same imaging system (e.g., X-ray machine 10). Another embodiment of step 45 includes moving the subject to a second position for image acquisition by a second imaging system 455 different and independent of the first imaging system 5. The step 450 can include automatically operating the table system 300 in association with multiple independent imaging systems 5, 455 (e.g., fluoroscopic, angiographic, CT, X-ray, MRI, etc.). For example, assuming the subject 8 can be supported by the table system 300 at a first position for image acquisition with the X-ray machine 10, step 450 can include automatically steering or guiding movement of the mobile device 310 of the table system 300 in support of the subject 8 for an oncology medical procedure along a pre-programmed path to a second position for image acquisition by second imaging system 455, which can be a CT scanner. The table system 300 can support the subject 8 while the portable mobile device 310 can automatically transport the subject 8 from the first position for imaging by the X-ray machine 10 to the second position for imaging by a CT scanner 452. The table system 300 can be operable to move the subject 8 between multiple imaging systems 5 and 452 or more in an automatic and a predictable path, with reduced risk to the subject 8, the caregivers, and the imaging systems 5 and 452.

Step 455 can include repeating one or more of the above steps to perform multiple image acquisitions in a pre-programmed switch or alternating sequence by the multiple imaging systems 5 and 405. Step 460 can include detecting or receiving an instruction of completion of the image acquisition or completion of the medical procedure on the subject 8. Step 465 can include steering or guiding movement of at least one of the mobile device 310 of the table system 300 or the mobile device 22 of the imaging system 5 or X-ray machine 10 to return to the pre-programmed park or store positions. Step 470 can include applying restraint of at least one of the table system 300 and the imaging system 5 or X-ray machine 10.

One or move of the above-described steps of the method 400 can be according to a pre-programmed protocol selected from a plurality of image acquisition protocols or therapeutic protocols dependent on an input or desired diagnosis received at the system 5. The preprogrammed protocol can include automatically causing application of the restraint force to the table system 300 in response to detecting proper alignment/position of the subject so as to ready for image acquisition. Likewise, the preprogrammed protocol can include causing automatic release of the restraint force in response to detecting complete of image acquisition at the current alignment/position.

Dependent on detection of a type of received command signal as a navigation or an orientation signal, step 450 can include computing if one or more of the above steps are being executed; storing or causing the navigation or orientation signal received at the navigation system 345 to sit idle without further processing; computing a check as to whether the execution of one or more of the above steps is terminated in order to authorize the processing of the navigation or orientation signal; and if no detection of execution of one or more of the above steps, authorizing further processing of this navigation or orientation signal. It should also be understood that one or more components of the navigation system 345 can be located at the table system 300 or mobile device 310 or be stationary in the room 12 and is not limiting on the subject matter described herein.

According to one embodiment, the imaging system 5 or the x-ray machine 10 can be automatically operated in the wireless manner described herein in combination with and independently of the table system 300 in support of the subject 8. The imaging system 5 or X-ray machine 10 can be shifted, moved or positioned in a working mode so that the table system 300 supports the subject 8 within the C-shape of the arm 14 such that to perform image acquisition of the subject 8. The subject matter described herein provides an imaging system 5 to perform imaging in wireless combination, yet independent and not interconnected with, a table system 300 where neither the imaging system 5 or table system 300 has a hardwire connection (e.g., electrical power cord or communication bus) to a stationary electrical connector 378 (e.g., wall socket or data connector) in the room 12.

Although the above description of the imaging system 5, X-ray machine 10, and method 400 are described with respect to medical diagnostic image acquisition of the subject 8 supported on the table system 300, it should be understood that the mobile device 310 and table system 300 can be employed in a variety of applications (e.g., airport screening, industrial or commercial applications, etc.) and is not limiting on the subject matter described herein.

Although certain embodiments of the system 5 and 300 are described above, it should be understood that every combination of aspects or features or components may not be described for sake of brevity, and that one or more various aspects or features or components of the system 5 can be combined with one or various aspects, features or components of the system 300, and vice versa, and is not limiting on the subject matter described herein. Also, features of one or more embodiments of the navigation system 324 or the wireless power system 380 described above can be combined and is not limiting of the subject matter described herein.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method of image acquisition of a subject supported from a floor, the method comprising the steps of:
providing a table system comprising a tabletop in support of the subject from the floor, and a mobile device having a drive to automatically transport the table system across the floor;
providing an imaging system operable to perform image acquisition of the subject, wherein the table system and the imaging system are configured to move (i) independently of each other, and (ii) in concert with each other so that at least one movement of one of said systems is automatically responsive to at least one movement of the other of said systems;

identifying a current position and calculating a path relative to a reference to a pre-programmed target position for image acquisition;

communicating an instruction to the table system to transport the table system via the mobile device along the path to the pre-programmed target position; and receiving wireless communication signals to steer movement of the mobile device of the table system in transport of the subject and to control movement of the imaging system.

2. The method of claim 1, further including the step of:
acquiring electrical power from a battery to drive to the mobile device.

3. The method of claim 1, further including the step of:
acquiring electrical power from a wireless power system to drive the mobile device, the wireless power system including an inductor transmitter to generate electrical power across an air gap to an inductor receiver attached at the table system.

4. The method of claim 1, further including the step of:
acquiring a current position information of the table system via a navigation system, and calculating a path to steer the mobile device in support of the table system to a target position.

5. The method of claim 4, wherein the target position is a preprogrammed position for image acquisition of the subject.

6. The method of claim 4, wherein the step of acquiring a current position information of the table system includes communicating across a wireless link, a type of wireless link including one of the group consisting of: optical, laser, infrared, radio frequency (rF), electromagnetic, high or low frequency sound, shape recognition, bar code recognition, and global positioning.

7. The method of claim 1, further including the step of:
receiving a wireless communication signal including a feedback that the table system is located at the target position for image acquisition.

8. The method of claim 1, further including the step of:
receiving a wireless communication signal to steer movement of the mobile device support of the table system to a target position in sequence relative to the transport of an imaging system across the floor via a second mobile device.

9. A system to perform image acquisition of a subject supported from a floor, the system comprising:

an imaging system operable to perform image acquisition of the subject; and a table system in mobile support of the subject from the floor, the table system comprising a mobile device comprising a drive, the table system in communication with a wireless navigation system to transport the subject across the floor, wherein the mobile device of the table system and the imaging system are configured to receive a wireless communication signals to steer movement of the mobile device with the drive and to control movement of the imaging system, and wherein the table system and the imaging system are configured to move (i) independently of each other, and (ii) in concert with each other so that at least one movement of one of said systems is automatically responsive to at least one movement of the other of said systems.

10. The system of claim 9, wherein the table system does not include a hardwire connection to a stationary electrical wall socket.

11. The system of claim 9, wherein the drive is connected to a battery located at the table system.

12. The system of claim 9, wherein the mobile device includes a drive to power the mobile device to move the table system across the floor, the drive connected to receive electrical power from a wireless power system, the wireless power system including an inductor transmitter separated by an air gap from a inductor receiver, wherein the inductor transmitter generates electrical power across the air gap at the inductor receiver, and wherein the inductor receiver is electrically connected to deliver the electrical power to the drive to move the table system across the floor.

13. The system of claim 9, wherein the mobile device includes a roller system having at least one guide wheel driven by the electrical drive and at least one free wheel.

14. The system of claim 9, wherein the table system calculates a path to transport the subject to a target position from a current position acquired by a navigation system.

15. The system of claim 14, wherein the target position is a preprogrammed position.

16. The system of claim 9, wherein the table system automatically transports the subject across the floor to a second target position for image acquisition in response to a feedback of completion of image acquisition at a first target position.

17. The system of claim 9, wherein the table system receives a wireless communication to instruct movement of the tabletop in support of the subject to one of a tilt position with respect to horizontal and a variable elevation with respect to the floor.

18. The system of claim 9, wherein the imaging system receives wireless signals to steer movement of the imaging system across the floor in sequence relative to wireless signals to steer movement of the table system in support of the subject across the floor.

19. The system of claim 9, wherein the movement of the imaging system across the floor operates automatically in a wireless manner independently of movement of the table system in a wireless manner across the floor.

20. The system of claim 9, wherein the imaging system and table system move in concert with one another in a generally simultaneous time frame.

* * * * *